(12) United States Patent
Bertoni

(10) Patent No.: US 10,745,153 B2
(45) Date of Patent: Aug. 18, 2020

(54) METHOD FOR THE PREPARATION OF CONTAINMENT UNITS OF BIOLOGICAL LIQUIDS

(71) Applicant: BIOMED DEVICE S.R.L., Reggello (IT)

(72) Inventor: Marco Bertoni, Modena (IT)

(73) Assignee: Biomed Device S.R.L., Reggello (IT)

( * ) Notice: Subject to any disclaimer, the term of this patent is extended or adjusted under 35 U.S.C. 154(b) by 78 days.

(21) Appl. No.: 16/216,945

(22) Filed: Dec. 11, 2018

(65) Prior Publication Data

US 2019/0127090 A1 May 2, 2019

Related U.S. Application Data

(63) Continuation of application No. 14/004,995, filed as application No. PCT/IB2012/000508 on Mar. 15, 2012, now abandoned.

(30) Foreign Application Priority Data

Mar. 16, 2011 (IT) .............................. MO2011A0058

(51) Int. Cl.
*B65B 3/00* (2006.01)
*A61M 1/02* (2006.01)

(52) U.S. Cl.
CPC ........... *B65B 3/003* (2013.01); *A61M 1/0231* (2014.02); *A61M 1/0272* (2013.01)

(58) Field of Classification Search
None
See application file for complete search history.

(56) References Cited

U.S. PATENT DOCUMENTS

| 4,015,628 A * | 4/1977 | Randolph | ............. B01F 3/1271 137/565.31 |
| 2005/0014273 A1 * | 1/2005 | Dahm | .................... B01J 19/249 436/45 |

FOREIGN PATENT DOCUMENTS

| DE | 19934491 A1 | 1/2001 |
| EP | 1930033 | 6/2008 |

(Continued)

OTHER PUBLICATIONS

International Search Report dated Jun. 4, 2012, corresponding to PCT/IB2012/000508.

*Primary Examiner* — Matthew D Krcha
(74) *Attorney, Agent, or Firm* — David B. Tingey

(57) ABSTRACT

The method for the preparation of containment units of biological liquids, comprises the following stages of: furnishing a device (1) comprising a main body (2) which defines at least a continuous filling channel (3), having at least an inlet gap (3a) of a biological liquid and at least an air outlet gap (3b), a plurality of containment units (4) arranged in succession to one another so as to communicate with each other and defining respective containment chambers (5) positioned along the filling channel (3) and placed in between the inlet gap (3a) and the outlet gap (3b), a hydrophobic air filtering device (6) associated with the body (2) in correspondence to the outlet gap (3b), wherein the containment units (4) are bulbous members each having opposing elastically deformable sides that define the respective containment chambers therebetween, and wherein after deformation the sides return to a convex non-deformed idle configuration in which the sides are at a non-zero distance from one another;
injecting a biological fluid along the channel (3) through the inlet opening (3a) so as to push towards outside the air contained inside the containment chambers (5) through the (Continued)

outlet gap (3*b*) and to gradually filling the containment chambers (5) which it crosses;
closing and isolating the containment units (4) the one from the other.

7 Claims, 2 Drawing Sheets

(56) References Cited

FOREIGN PATENT DOCUMENTS

WO     2006/078796 A2    7/2006
WO     2010/122542 A1    10/2010

* cited by examiner

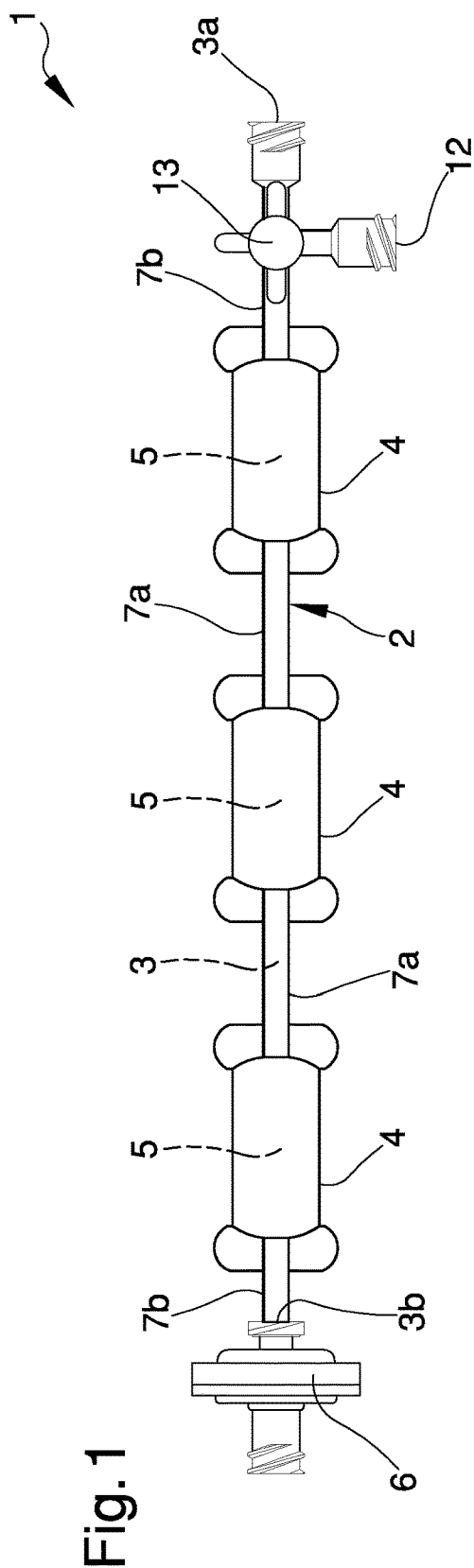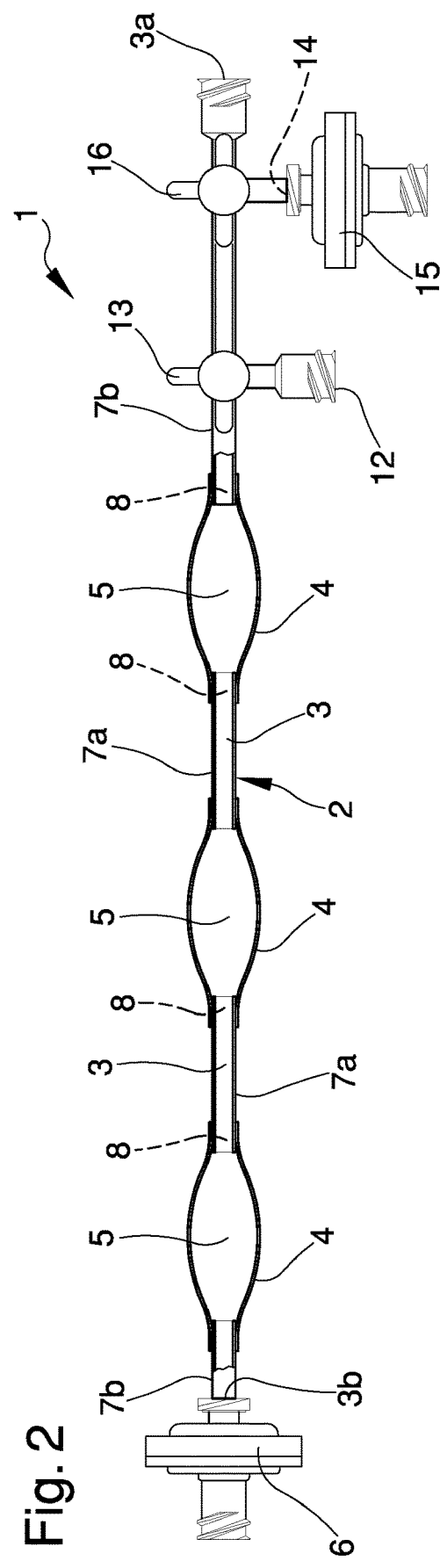

METHOD FOR THE PREPARATION OF CONTAINMENT UNITS OF BIOLOGICAL LIQUIDS

CROSS-REFERENCE TO RELATED APPLICATION

This is a continuation application that claims priority to U.S. utility application Ser. No. 14/004,995, entitled Device for the Preparation of Containment Units of Biological Liquids, filed Nov. 12, 2013, which claims priority to PCT/IB2012/000508, entitled Device for the Preparation of Containment Units of Biological Liquids, filed Mar. 15, 2012, which claims foreign priority to Italian Application No. MO2011A000058, filed Mar. 16, 2011; the entire disclosures of which are incorporated herein by reference.

TECHNICAL FIELD

The present invention relates to a method for the preparation of containment units of biological liquids.

BACKGROUND ART

Generally speaking, to fill containment units of biological liquids such as stem cells, platelet concentrates, serum eye drops, plasma, etc . . . , devices of known type are used having means for the connection of a syringe containing the biological liquid and a plurality of containment units to be filled.

More in particular, these connection means define a transit channel for the biological liquid having an inlet gap, connectable to the syringe containing the biological liquid, and a plurality of outlet gaps, associable with the units to be filled.

These devices also comprise at least a mouth for expelling the air contained in the containment units, and aspired by means of a syringe. In fact, the containment units generally used with these devices of known type are of the soft or flexible type, i.e., deformable to such an extent as to make their opposite sides coincide with one another, so that by applying a suitable vacuum, they can be emptied of the air contained inside them, thereby making subsequent filling easier.

Some of these devices of known type are described by DE 19934491 and by EP 1930033.

These devices of known type do however have a number of drawbacks.

They are in fact complicated to make and assemble, also due to the high number of parts making them up.

Another drawback of these known devices consists in the fact that they take a long time to prepare. These long preparation times are due at least in part to the carrying out of the air aspiration and biological liquid filling phases, which may even have to be repeated several times in order to eliminate as much air as possible, and to the handling of the devices themselves aimed at facilitating the movement of the air bubbles towards the outlet mouth.

Another problem still of devices of known type consists in the fact that they do not allow the easy preparation of a high number of containment units, e.g., more than twenty units, due to the ensuing difficulty in handling same.

Furthermore, the larger the number of containment units to be filled, the greater the dimensions must be of the connecting elements placed between the syringe and the containment units themselves, hence the biological liquid which remains inside such connecting elements and which is wasted increases along with the increase in the number of units to be filled.

Another drawback of known devices consists in the fact that they can only be used with containment units of a soft or flexible type, i.e., whose walls are deformable until they coincide with one another.

The devices of known type cannot therefore be used with semi-rigid containment units, i.e., deformable but not enough to cause their collapse, although preferable to soft bags inasmuch as they permit controlling the dispensing of the biological liquid towards the outside in a more precise and easier way.

More in detail, the semi-rigid units are not used with the aforementioned devices of known type inasmuch as they cannot be completely emptied of the air contained inside them, and which therefore prevents them from being completely filled. The biological liquid introduced into the transit channel by the syringe manages to return up towards the semi-rigid containment units only along a section of the channel itself due to the presence of air which prevents it from moving any further forward.

It therefore follows that the devices of known type for filling containment units of biological liquids, such as stem cells, platelet concentrates, serum eye drops, plasma, etc . . . , have a range of application limited only to the use of flexible containment units, which are however to be considered worse than the semi-rigid type inasmuch as they do not permit the controlled dispensing of the biological liquid itself.

DESCRIPTION OF THE INVENTION

The main aim of the present invention is to provide a method for the preparation of containment units of biological liquids which is considerably more simple to make and use than the known devices.

Within this aim, one object of the present invention is to provide a method which allows to fill a plurality of containment units in a considerably quicker way than the known devices.

One object of the present invention is to provide a method which has a greater flexibility of use, meaning that it can be used indifferently for filling flexible, semi-rigid or rigid containment units.

Another object of the present invention is to provide a method for the preparation of containment units of biological liquids which allows overcoming the mentioned drawbacks of the state of the art within the ambit of a simple, rational, easy and effective to use as well as low cost solution.

The above objects are achieved by the present wherein it comprises the following stages of:
furnishing a device (1) comprising a main body (2) which defines at least a continuous filling channel (3), having at least an inlet gap (3a) of a biological liquid and at least an air outlet gap (3b), a plurality of containment units (4) arranged in succession to one another so as to communicate with each other and defining respective containment chambers (5) positioned along said filling channel (3) and placed in between said inlet gap (3a) and said outlet gap (3b), a hydrophobic air filtering device (6) associated with said body (2) in correspondence to said outlet gap (3b), wherein said containment units (4) are bulbous members each having opposing elastically deformable sides that define the respective containment chambers therebetween, and wherein after deformation the sides return to a convex non-deformed idle configuration in which the sides are at a non-zero distance from one another;

injecting a biological fluid along said channel (3) through said inlet opening (3a) so as to push towards outside the air contained inside said containment chambers (5) through the outlet gap (3b) and to gradually filling the containment chambers (5) which it crosses;

closing and isolating said containment units (4) the one from the other.

BRIEF DESCRIPTION OF THE DRAWINGS

Other characteristics and advantages of the present invention will become more evident from the description of a preferred, but not sole, embodiment of a device for the preparation of containment units of biological liquids, illustrated purely as an example but not limited to the annexed drawings in which:

FIG. 1 is a plan view from above of a device according to the invention in a first embodiment;

FIG. 2 is a transversal section of the device of FIG. 1;

EMBODIMENTS OF THE INVENTION

Figure 3:
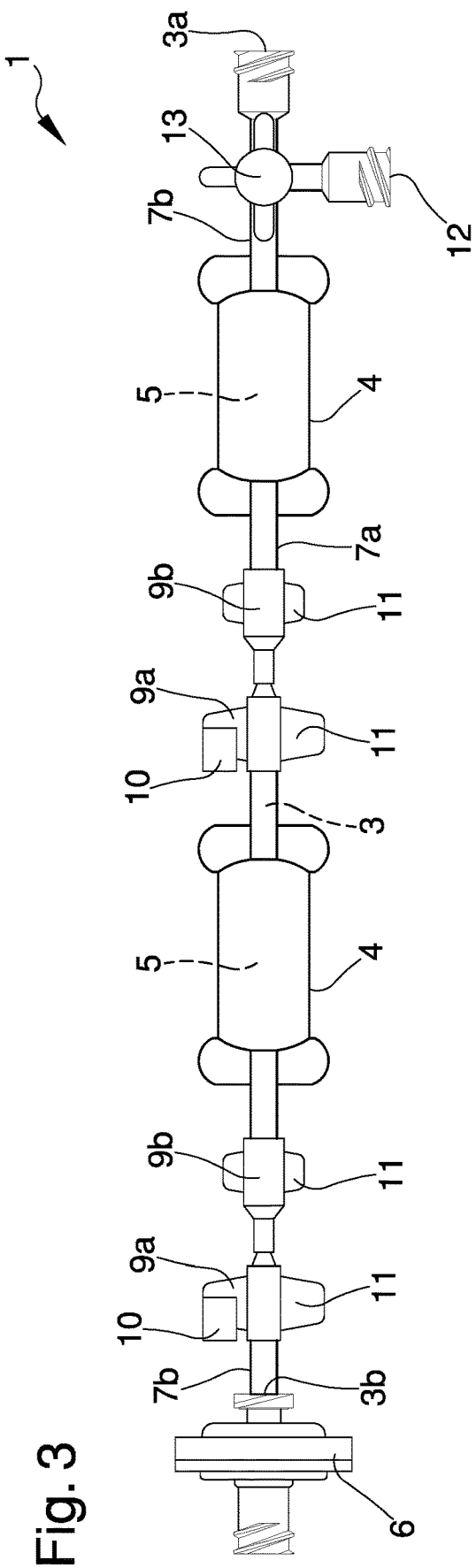
FIG. 3 is a plan view from above of a device according to the invention in a second embodiment.

With particular reference to such figures, globally indicated by 1 is a device for the preparation of containment units of biological liquids, such as stem cells, platelet concentrates, serum eye drops, plasma, etc. . . . . .

According to the invention, the device 1 comprises at least one main body 2 which defines at least a filling channel 3 having an inlet gap 3a, connectable to a syringe containing a biological liquid, and at least an outlet gap 3b for air expulsion.

Moreover, the body 2 comprises a plurality of containment units 4, arranged in succession to one another, which define respective containment chambers 5 positioned along the channel 3 and placed in between the inlet gap 3a and the outlet gap 3b.

The chambers 5 communicate therefore with the filling channel 3. More in particular, the chambers 5 communicate with the inlet gap 3a and outlet gap 3b.

More in detail, the inlet gap 3a and the outlet gap 3b are arranged in correspondence to the opposite extremity sections of the body 2. The inlet gap 3a and the outlet gap 3b are therefore arranged on opposite sides with respect to the containment units 4.

The units 4 can be of the soft, semi-rigid or rigid type.

Preferably, the units 4 are of the semi-rigid type. More in particular, the units 4 are elastically deformable, and so they naturally tend to return to an idle configuration wherein the walls delimiting the relative chambers 5 are at a distance from one another.

The body 2 comprises, in correspondence to the inlet gap 3a, a connection of the luer lock type.

Furthermore, the device 1 comprises a filtering device 6 of hydrophobic type associated with the body 2 in correspondence to the outlet gap 3b.

Advantageously, the body 2 comprises at least an intermediate tubular element 7a placed in between each pair of consecutive containment units 4 and at least two extremal tubular elements 7b associated with the first and last of the units 4 respectively and defining the inlet gap 3a and the outlet gap 3b. Each tubular element 7a and 7b therefore defines a corresponding section of the filling channel 3.

More in particular, each unit 4 has two openings 8, arranged on opposite sides, each of which is associated with a respective intermediate or extremal tubular element 7a and 7b.

Preferably, the units 4 are made separately with respect to the tubular elements 7a and 7b and are associated integral with the latter in correspondence to their extremal portions.

Different embodiments cannot be ruled wherein the units 4 are made in a single body piece with the tubular elements 7a and 7b.

In the second embodiment shown in the FIG. 3, at least one of the tubular elements 7a and 7b comprises a first and a second portion 9a and 9b associated integral the one with the other and crossed by the filling channel 3. More in particular, the first portion 9a is separable from the second portion 9b so as to interrupt the filling channel 3 and define an outlet mouth for the biological liquid on the second portion itself. Suitably, the first portion 9a comprises closing means 10 for closing the outlet mouth so defined on the second portion 9b.

Preferably, the first portion 9a is removable by tearing off from the second portion 9b and separation means 11 are provided for separating the portions 9a and 9b. More in detail, the separation means 11 comprise two pairs of fins, of which one pair is associated with the first portion 9a and the other pair is associated with the second portion 9b, suitable for being gripped by an operator to facilitate the reciprocal rotation of the portions 9a and 9b.

Suitably, the units 4 have bigger section than the tubular elements 7a and 7b. Advantageously, the channel 3 also comprises at least an additional mouth 12 associable with an additional syringe, e.g., for the introduction of substances for activating the biological liquid.

In the first and in the second embodiments shown in the FIGS. 1, 2 and 3, the additional mouth 12 is arranged on the opposite side of the outlet gap 3*b* with respect to the containment units 4. More in detail, the additional mouth 12 is defined on the extremal tubular element 7*b* which also defines the inlet gap 3*a*. In these embodiments, the device 1 comprises at least one valve element 13 associated with the body 2 and which can be operated to place selectively in communication the containment chambers 5 with the inlet gap 3*a* or with the additional mouth 12.

In the third embodiment shown in FIG. 4, instead, the additional mouth 12 is defined on at least one intermediate tubular element 7*a*. More in particular, in this embodiment, the channel 3 comprises a plurality of additional mouths 12 defined on each intermediate tubular element 7*a* and on at least one extremal tubular element 7*b*. Preferably, the device 1 also comprises at least one elastically deformable valve body arranged in correspondence to each additional mouth 12; such valve body, not visible in detail in the figures, is suitable for opening by effect of the insertion of the additional syringe needle and for closing automatically following the removal of the latter.

Advantageously, as shown in FIG. 2, the channel 3 also comprises one additional gap 14 suitable for allowing air to come out in the event of two or more syringes being used for filling the units 4.

Suitably, the additional gap 14 is arranged on the opposite side of the outlet gap 3*b* with respect to the units 4.

More in particular, the additional gap 14 is defined along the extremal tubular element 7*b* which also defines the inlet gap 3*a*.

In the embodiment shown in FIG. 2, the additional gap 14 is distinct from the inlet gap 3a, the outlet gap 3b and the additional mouth 12.

The device 1 then comprises a further filtering device 15, this too of the hydrophobic and breathable type, associated with the body 2 and fitted in the additional gap 14.

Furthermore, the device 1 comprises a further valve element 16 associated with the body 2 in correspondence to the additional gap 14 and which can be operated to place selectively in communication the inlet gap 3a with the additional gap 14 or with the chambers 5.

The operation of the present invention is the following.

Initially, a syringe is introduced containing a biological liquid inside the inlet gap 3a and the biological liquid is injected along the channel 3 by pressing the piston of the syringe itself.

The biological liquid injected this way runs along the entire channel 3 and gradually fills the containment chambers 5 which it crosses.

Before injecting the biological liquid along the channel 3, there is air inside the chambers 5 and the tubular elements 7a and 7b. As the biological liquid moves forward, this air volume is pushed towards the outlet gap 3b, and consequently as the biological liquid moves forward inside the channel 3, the air initially present along the filling channel itself escapes outside the body 2.

If it then becomes necessary to introduce one or more activating substances, such as autologous and homologous thrombin and batroxobin in the case of platelet concentrates, inside the units 4, the relative syringe is introduced into the additional mouth 12 thus injecting its contents along the channel 3.

In the first and in the second embodiment shown in the FIGS. 1, 2 and 3, there is just one additional mouth 12 and, therefore, the activation substance must be injected in the chambers 5 before these are closed.

Figure 4:
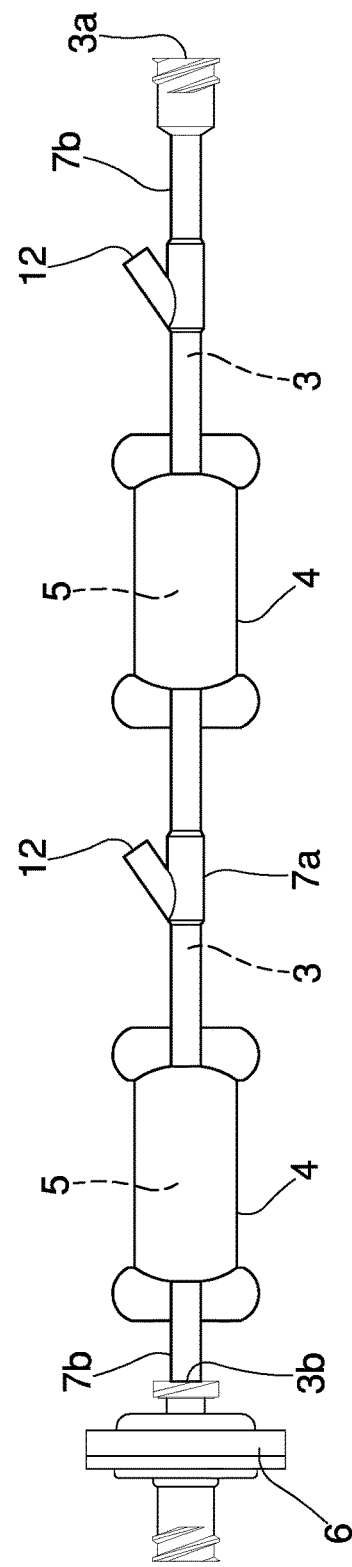
FIG. 4 is a plan view from above of a device according to the invention in a third embodiment.

In the third embodiment shown in FIG. 4, on the other hand, each intermediate tubular element 7a and one extremal tubular element 7b is provided with a relevant additional mouth 12, and so the activation substances can also be injected inside the chambers 5 after each chamber 5 has been closed.

Once all the units 4 have been filled with biological liquid, these are closed and isolated the one from the other.

More in particular, in the embodiments described above, the units 4 are closed by means of a welding long each tubular element 7a and 7b. At this point, each unit 4 can be separated from the others and managed independently.

As regards the second embodiment described and shown in FIG. 3, the closing of each tubular element 7a and 7b is suitably done in correspondence to the relative first portion 9a, in such a way that this can then be detached from the corresponding second portion 9b to close it.

It has in point of fact been ascertained how the described invention achieves the proposed objects and in particular the fact is underlined that it allows preparing a plurality of containment units of biological liquids in a considerably more simple and practical way compared to devices of known type.

In fact, the positioning of the containment units in series along an open channel allows automatically expelling the air inside the channel itself by effect of the introduction of the biological liquid.

Again, the method according to the invention can be used with any type of containment units, meaning both with soft containment units and with semi-rigid or rigid ones.

Furthermore, the method according to the invention allows filling any number of containment units in a very easy way, without this affecting at all its ease of handling.

The invention claimed is:

1. A method for the preparation of containment units of biological liquids, wherein it comprises the following stages of:
    furnishing a device (1) comprising a main body (2) which defines at least a continuous filling channel (3), having at least an inlet gap (3a) of a biological liquid and at least an air outlet gap (3b), a plurality of containment units (4) arranged in succession to one another so as to communicate with each other and defining respective containment chambers (5) positioned along said filling channel (3) and placed in between said inlet gap (3a) and said outlet gap (3b), a hydrophobic air filtering device (6) associated with said body (2) in correspondence to said outlet gap (3b), wherein said containment units (4) are bulbous members each having opposing elastically deformable sides that define the respective containment chambers therebetween, and wherein after deformation the sides return to a convex non-deformed idle configuration in which the sides are at a non-zero distance from one another;
    injecting a biological fluid along said channel (3) through said inlet opening (3a) so as to push towards outside the air contained inside said containment chambers (5) through the outlet gap (3b) and to gradually filling the containment chambers (5) which it crosses;
    closing and isolating said containment units (4) the one from the other.

2. The method according to claim 1, wherein it comprises the stage of separating said containment units (4) the one another after said stage of closing and isolating, said containment nits (4) being configured to be a separate single, elastically deformable, containment unit from which the biological liquid is dispensed when elastically deformed.

3. The method according to claim 1, wherein said filling channel (3) comprises at least one additional mouth (12) and wherein it comprises at least the stage of introducing one or more activating substances into said additional mouth (12).

4. The method according to claim 1, wherein said closing and isolating is carried out by means of a welding.

5. The method according to claim 4, wherein said body (2) comprises at least an intermediate tubular element (7a) placed in between each pair of consecutive containment units (4) and at least two extremal tubular elements (7b) associated with the first and last of said containment units (4) respectively and defining said inlet gap (3a) and said outlet gap (3b), and wherein said closing and isolating is carried out by means of a welding long each of said tubular elements (7a, 7b).

6. The method according to claim 5, wherein at least one of said tubular elements (7a, 7b) comprises a first and a second portion (9a, 9b) associated integral the one with the other and crossed by said filling channel (3), said first portion (9a) being separable from said second portion (9b) so as to interrupt the filling channel (3) and define an outlet mouth for the biological liquid on the second portion itself, and wherein said closing of each tubular element (7a, 7b) is suitably done in correspondence to the relative first portion (9a), in such a way that this can then be detached from the corresponding second portion (9b) to close it.

7. The method according to claim 1, wherein said injecting a biological fluid is carried out by means of a syringe.

* * * * *